United States Patent
Eiriksson

(10) Patent No.: US 8,974,731 B2
(45) Date of Patent: Mar. 10, 2015

(54) SAMPLE CARRIER AND/OR SAMPLE CARRIER PROCESSING APPARATUS

(75) Inventor: Ari Eiriksson, South Hamilton, MA (US)

(73) Assignee: Analogic Corporation, Peabody, MA (US)

( * ) Notice: Subject to any disclaimer, the term of this patent is extended or adjusted under 35 U.S.C. 154(b) by 452 days.

(21) Appl. No.: 13/197,969

(22) Filed: Aug. 4, 2011

(65) Prior Publication Data

US 2013/0032481 A1 Feb. 7, 2013

(51) Int. Cl.
*G01N 27/00* (2006.01)
*G01N 31/00* (2006.01)
*G01N 33/00* (2006.01)
*B01L 3/00* (2006.01)
*G01N 33/559* (2006.01)
*G01N 1/00* (2006.01)
*G01N 1/22* (2006.01)

(52) U.S. Cl.
USPC ............. 422/63; 422/502; 422/504; 422/537; 204/450; 204/461; 204/600; 73/863; 73/863.01; 73/863.11; 73/863.72

(58) Field of Classification Search
USPC .......................... 422/502, 504; 73/863, 863.1
See application file for complete search history.

(56) References Cited

U.S. PATENT DOCUMENTS

| | | | |
|---|---|---|---|
| 6,528,006 B1 | 3/2003 | Jansen | |
| 6,613,581 B1* | 9/2003 | Wada et al. | 436/518 |
| 7,125,729 B2 | 10/2006 | Burger et al. | |
| 7,159,618 B2* | 1/2007 | Broyer et al. | 137/828 |
| 7,166,186 B2 | 1/2007 | Lowry | |
| 7,223,315 B2 | 5/2007 | Chen | |
| 7,316,936 B2 | 1/2008 | Lowry | |
| 2007/0092409 A1* | 4/2007 | Beatty et al. | 422/100 |
| 2007/0231216 A1* | 10/2007 | Park et al. | 422/103 |
| 2012/0238032 A1* | 9/2012 | Durniak et al. | 436/164 |

FOREIGN PATENT DOCUMENTS

JP 2002036196 A * 2/2002

* cited by examiner

*Primary Examiner* — Jill Warden
*Assistant Examiner* — Julie Tavares
(74) *Attorney, Agent, or Firm* — Anthony M. Del Zoppo, III; Driggs, Hogg, Daugherty & Del Zoppo Co. LPA

(57) ABSTRACT

A sample processing apparatus includes a sample carrier receiving region configured to receive a sample carrier. The sample carrier includes at least one sample channel carrying at least one sample, at least one agent chamber carrying at least one agent to be moved to the at least one sample channel to facilitate processing of the at least one sample, and the at least one agent chamber includes at least one chamber cover covering at least one opening of the at least one agent chamber, inhibiting flow of the at least one agent from the at least one agent chamber to the at least one sample channel. The sample processing apparatus further includes a chamber opener configured to facilitate opening the at least one chamber cover. The sample processing apparatus further includes a fluid mover that moves the agent out of the at least one agent chamber after the at least one chamber cover is opened and into the at least one sample channel.

20 Claims, 7 Drawing Sheets

# SAMPLE CARRIER AND/OR SAMPLE CARRIER PROCESSING APPARATUS

TECHNICAL FIELD

The following generally relates to a sample carrier and/or a sample carrier processing apparatus configured to process one or more samples carried by the sample carrier, and more particularly to moving a fluid within the sample carrier.

BACKGROUND

Micro channel devices include, but are not limited to, devices which carry one or more samples for processing and/or analysis by a sample processing apparatus. Such devices have included, for each sample, at least one processing channel and one or more processing agent chambers, etc. One approach for moving a processing agent from an agent chamber to a processing channel has included using pressurized air. A DNA sequencer is a sample processing apparatus that can determine an order of the nucleotide bases (adenine, guanine, cytosine, and thymine) in a DNA sample. Generally, the sample is carried by a micro channel device such as a biochip, a lab-on-a-chip, or the like. The DNA sample is controllably moved through the processing channel where it is processed. Reagents, wash solutions, primers, dyes, and/or other agents have been moved from the agent chambers to the processing channel to facilitate processing the sample via pressurized air.

By way of example, with one DNA sequencer a bucchal swab with a bio-sample is processed to extract one or more DNA strands. An extraction fluid such as a lyses reagent is moved, via pressurized air, from an agent chamber to the channel for the extraction. The DNA strand is then moved to a purification region of the micro channel device where a purification fluid, such as a wash solution, is moved, via pressurized air, from an agent chamber to the channel for purification. The DNA strand is then moved to a replication (thermocycling amplification) region where the DNA strand is replicated and labeled via polymerase chain reaction (PCR). Replication and labeling fluids such as a primer and fluorescent dyes are moved, via pressurized air, from agent chambers to the channel for replication and labeling. The processed DNA strand is then moved to a separation and analysis region where the nucleotides are separated via electrophoresis and analyzed via an optical detection system.

Generally, each agent chamber has an entrance and exit that are initially closed with thin plastic material covers, which can be opened by exposing the covers to the pressurized air. However, achieving uniform material thickness and burst strength of the covers for corresponding chambers across channels is difficult, and the covers are expected to burst under a fairly wide range of pressures. This can be problematic since in a multi-channel chip it is not practical to break a large number of covers at the same time with individually controlled air supply lines. Another approach uses a common air supply line. However, the agents in the chambers in which the covers have been opened at a lower pressure must be prevented from moving while the pressure rises higher to burst open the covers of other chambers until all of the covers have been opened. Unfortunately, this may introduce a risk of premature release of fluid into process for some samples before others, causing non-uniformity in the process. Generally, the covers should be weak enough to be readily broken with reasonable levels of air pressure, but strong enough to sustain vibration and shock during shipping and handling. These conflicting requirements may put potentially costly constraints on the covers.

SUMMARY

Aspects of the application address the above matters, and others.

In one aspect, a sample processing apparatus includes a sample carrier receiving region configured to receive a sample carrier. The sample carrier includes at least one sample channel carrying at least one sample, at least one agent chamber carrying at least one agent to be moved to the at least one sample channel to facilitate processing of the at least one sample, and the at least one agent chamber includes at least one chamber cover covering at least one opening of the at least one agent chamber, inhibiting flow of the at least one agent from the at least one agent chamber to the at least one sample channel. The sample processing apparatus further includes a chamber opener configured to facilitate opening the at least one chamber cover. The sample processing apparatus further includes a fluid mover that moves the agent out of the at least one agent chamber after the at least one chamber cover is opened and into the at least one sample channel.

In another aspect, a method includes receiving a sample carrier in a sample carrier receiving region of a sample processing apparatus. The sample carrier includes at least one sample channel configured to carry at least one sample, at least one agent chamber carrying an at least one agent to be moved to the at least one sample channel to facilitate processing of the at least one sample, and the at least one agent chamber includes at least one chamber cover covering at least one opening of the at least one agent chamber, inhibiting flow of the at least one agent from the agent chamber to the at least one sample channel. The method further includes actuating a chamber opener of the sample processing apparatus to facilitate opening the at least one chamber cover. The method further includes actuating a fluid mover of the sample processing apparatus to move the at least one agent out of the at least one agent chamber after the chamber cover is opened and into the at least one sample channel of the sample carrier.

In another aspect, a sample carrier includes at least one sample channel and at least one agent chamber holding an agent with an entrance port and an exit port and first and second chamber covers respectively covering the entrance and exit ports. The first and second chamber covers inhibit fluid from entering the agent chamber and the agent from exiting the agent chamber. The first and second chamber covers include a material that melts in response to being illuminated with illumination for a pre-determined time duration, allowing the fluid to enter the agent chamber to displace the agent from the agent chamber and into the at least one sample channel.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
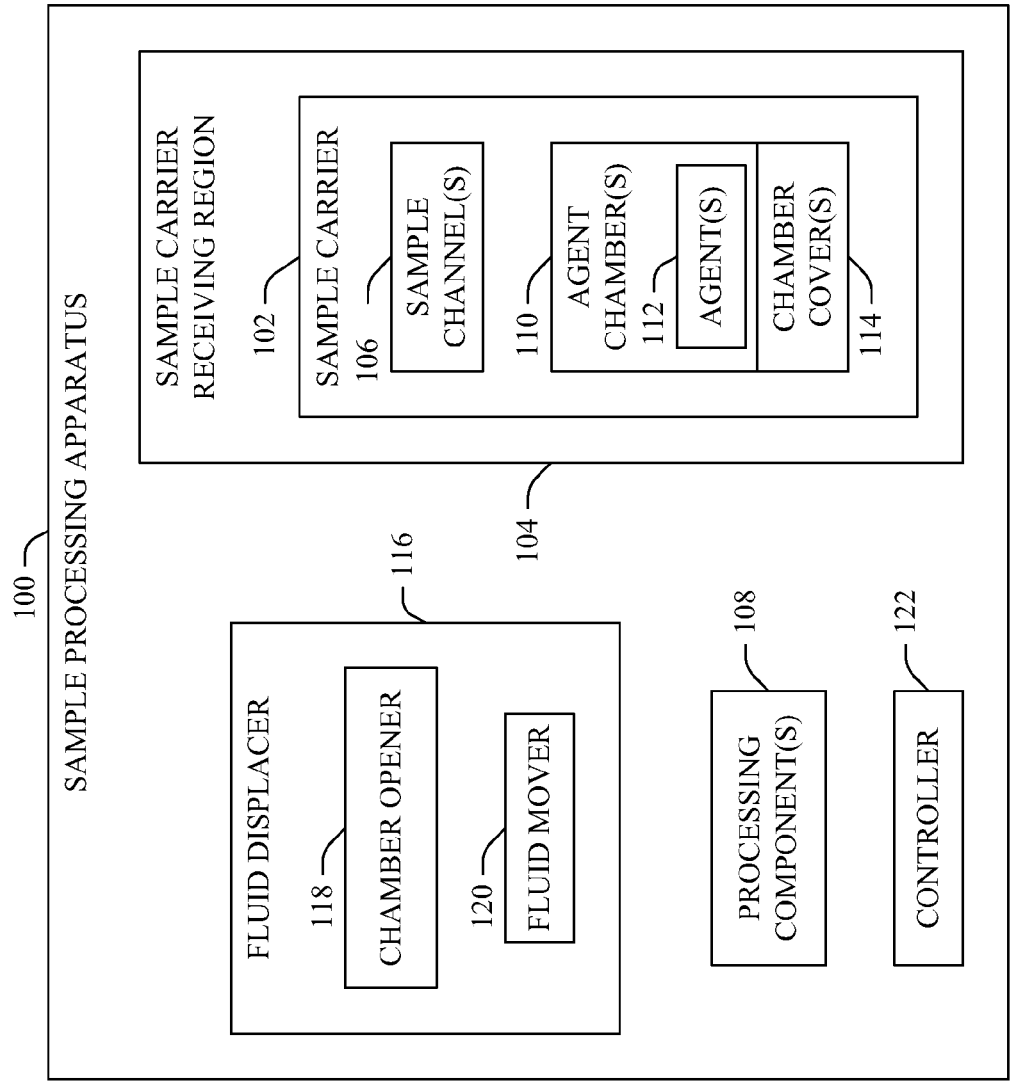
FIG. 1 schematically illustrates a sample processing apparatus and a sample carrier.

FIG. 1 schematically illustrates a sample processing apparatus 100 configured to process one or more samples carried by a micro channel device, such as a sample carrier 102, installed or inserted into a sample carrier receiving region 104 of the sample processing apparatus 100. In the illustrated embodiment, the sample processing apparatus 100 is configured to process DNA samples carried by the sample carrier 102. Additionally or alternatively the sample processing apparatus 100 can process other samples such as bio-samples and/or non-bio-samples. The sample carrier 102 can be a biochip, a lab-on-a-chip, and/or other micro channel device.

The illustrated sample carrier 102 includes one or more sample channels 106 which are configured to carry different samples, which are concurrently processed by individual processing stations 108 of the sample processing apparatus 100. Where configured for DNA analysis and the sample is a DNA sample, the processing stations 108 are configured to perform operations such as extract and purify DNA fragments, replicate and label the fragments with fluorescent dyes, separate the labeled fragments based on fragment size via electrophoresis, scan the fragments via an optical detection system, and determine allele numbers for the DNA samples.

The illustrated sample carrier 102 further includes one or more agent chambers 110, which are configured to carry one or more processing agents 112 used to facilitate processing samples. Examples of suitable agents include, but are not limited to, reagents, wash solutions, primers, dyes, etc. In this example, at least one of the agent chambers 110 includes one or more openings and one or more membranes or chamber covers 114 that cover the one or more openings. Generally, the chamber covers 114 include a thin and partially transparent plastic. In one instance, at least one of the chamber cover includes built-in tensile membrane stress, which assist the cover opener in the opening of the at least one chamber cover. As described in greater detail below, the one or more chamber covers 114 are configured so that they can be selectively opened, allowing for controlled ingress of a mover fluid (e.g., air, a gas, a gel, a liquid, etc.) into the chambers 110 and egress of the agent contained in the agent chambers 110 out of the agent chambers 110 and into the sample channels 106.

A fluid displacer 116 includes a chamber opener 118 and a fluid mover 120. The chamber opener 118 is used to selectively open a chamber cover 110. As described in greater detail below, in one instance, the chamber opener 118 a laser, a light emitting diode (LED), and/or other source of electromagnetic radiation, which can produce radiation that can structurally compromise (e.g., burst or break) the chamber covers 114. Also described below, the chamber opener 118 alternatively uses such a device to weaken (and not break) the chamber covers 114. The fluid mover 120 is then used to apply a force to the agents in the agent chambers 110 through the opened chamber covers 114 or to first open the weakened chamber covers 114 and then apply the force to the agents. The applied force urges the agents to flow out of other opened chamber covers 114 and into the sample channels 106. The force can be applied via gravity, pressurized air, gel, liquid, and/or otherwise.

It is to be appreciated that the processing apparatus 100 can be a hand-held, portable apparatus that can be readily carried by an operator. In this configuration, the processing apparatus 100 can be carried and employed at the location where the sample is collected, if desired, or elsewhere. The processing apparatus 100 may also be configured such that the operator can operate it with one hand. In another embodiment, the processing apparatus 100 is configured to be a stationary apparatus mounted to or placed on a table, the floor, etc. in a laboratory, office, or the like. In such a configuration, the processing apparatus 100 may be configured to remain at a particular location and process sample carriers 102 loaded therein.

Figure 2:
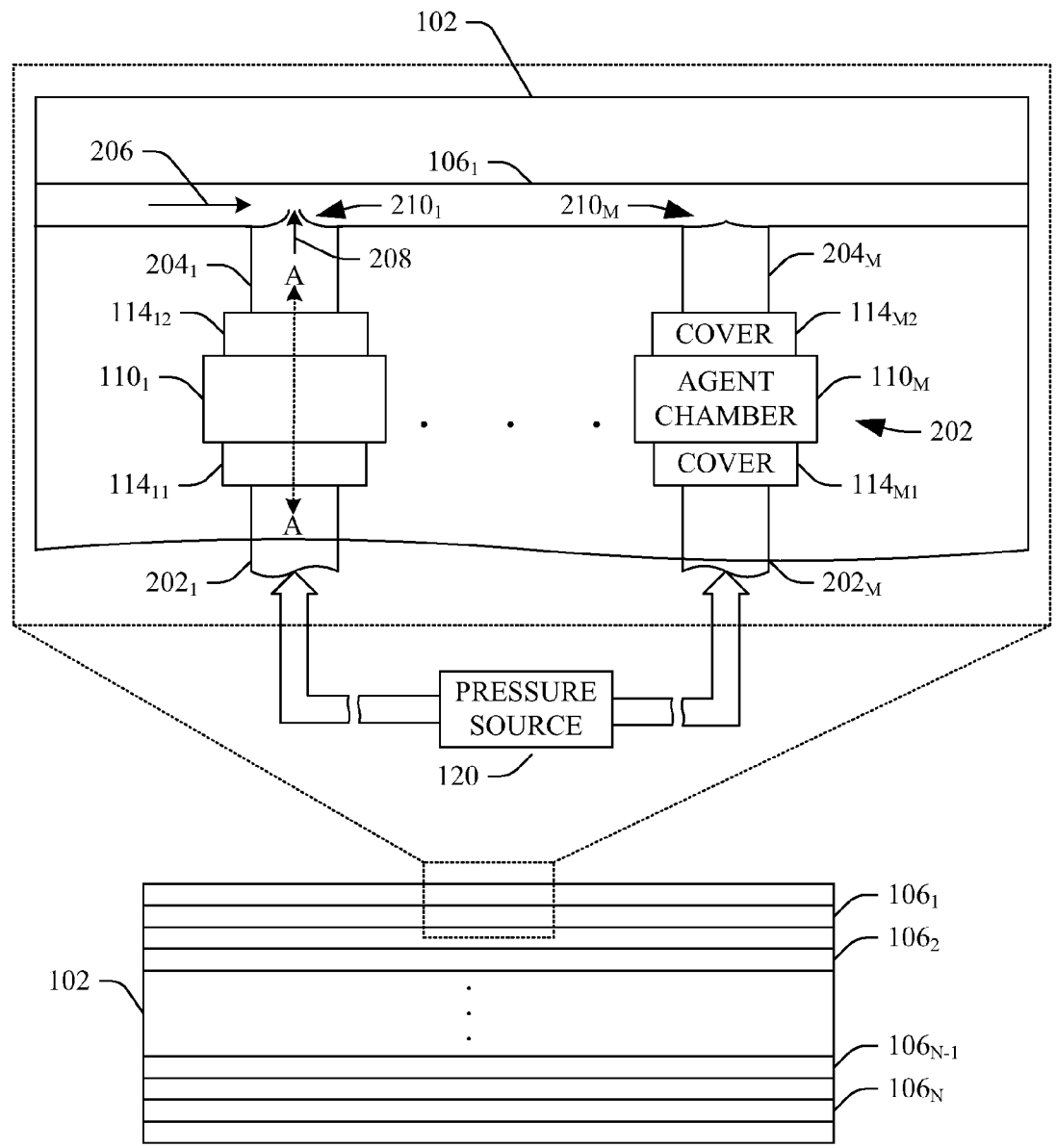
FIG. 2 schematically illustrates a top down view of a portion of the sample carrier, including an agent chamber and an agent chamber cover, and a portion of the sample processing apparatus, including an example fluid mover.
Figure 3:
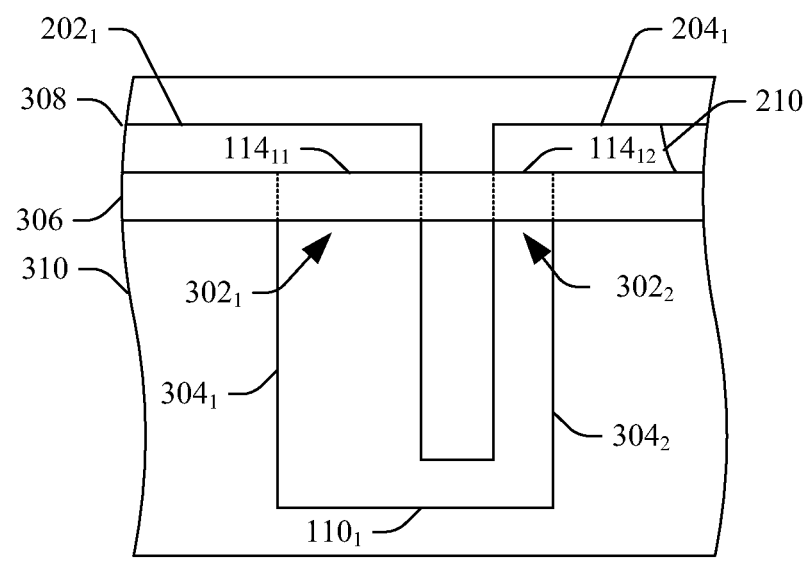
FIG. 3 schematically illustrates an example cross sectional view of the portion of the sample carrier, including the agent chamber and the agent chamber cover.
Figure 4:
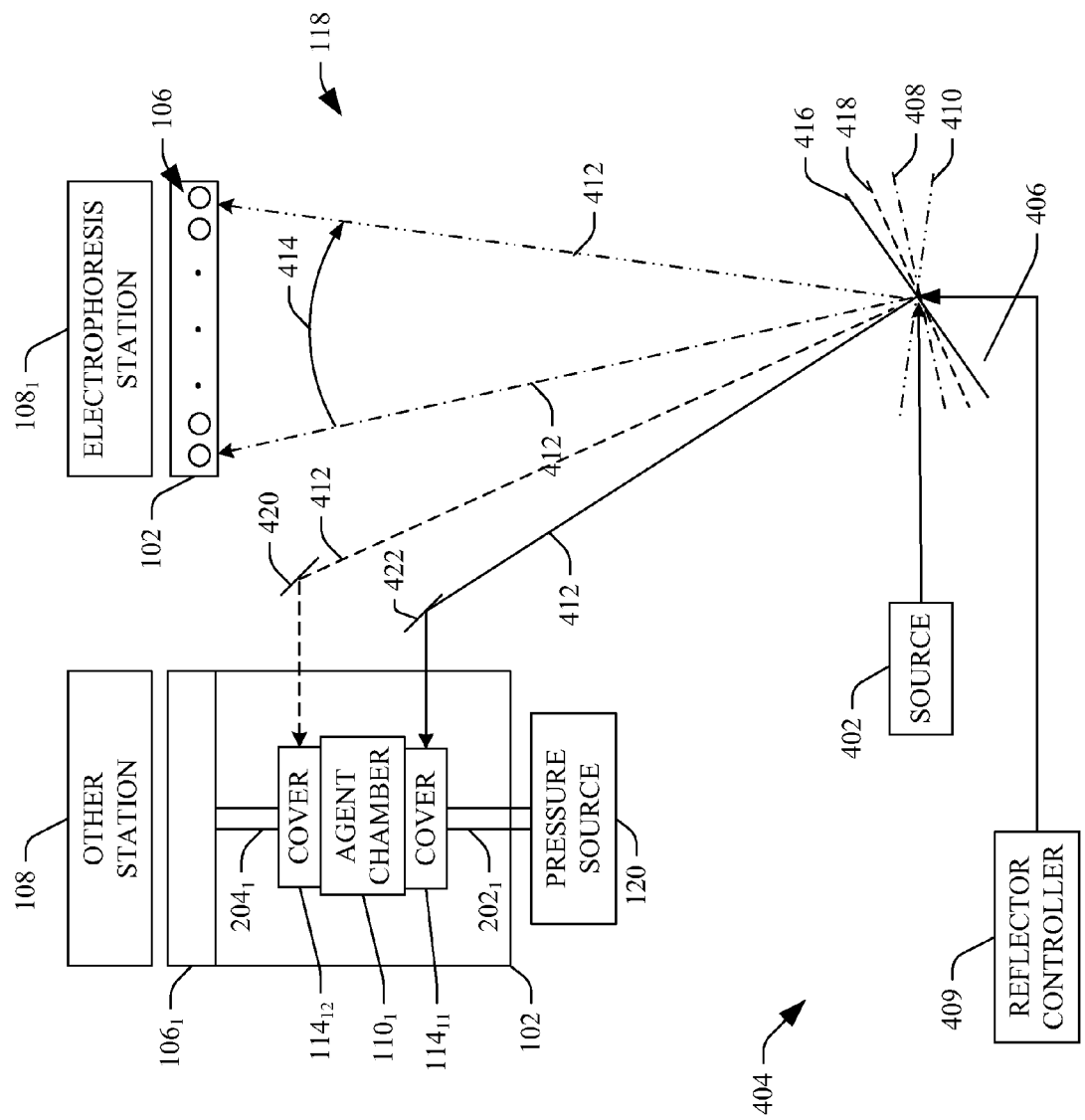
FIG. 4 schematically illustrates a portion of the sample processing apparatus, including an agent chamber cover opener.

FIGS. 2, 3 and 4 schematically illustrate an example of the sample carrier 102 and the sample processing apparatus 100. More particularly, FIGS. 2 and 3 respectively schematically illustrate a top down view and a cross sectional view of a portion of the sample carrier 102 showing the chamber covers 114, and FIG. 4 schematically illustrates an example chamber opener 118 in connection with the sample carrier 102.

Initially referring to FIG. 2, the illustrated sample carrier 102 includes a plurality of sample channels $106_1$, $106_2$, ..., $106_{N-1}$, $106_N$, where N is an integer equal to or greater than one. At least one of the sample channels 106 (sample channel $106_1$ in this example) is configured to receive at least one agent from at least a first set 202 of agent chambers $110_1$, ..., $110_M$, where M is an integer equal to or greater than one. Each of the agent chambers $110_1$, ..., $110_M$ includes multiple chamber covers $114_{11}$ and $114_{12}$, ..., $114_{M1}$ and $114_{M2}$ $110_M$. As briefly discussed above, the chamber covers 114 cover the openings of the agent chambers 114, which facilitates containing agents in the agent chambers 114.

As shown in FIG. 2, the fluid mover 120 includes a pressure source, which is in fluid communication with agent chamber entrance ports $202_1$, ..., $202_M$ (collectively referred to herein an entrance ports 202). (It is to be understood that the relative location, size, shape, etc. of the pressure source 120 is for illustrative purposes and not limiting.) The pressure source is configured to supply a pressure in a range between three (3) and ten (10) pounds per square inch (psig), such as four (4), five (5) or six (6) psig.

The sample channel $106_1$ is in fluid communication with agent chamber exit ports $204_1$, ..., $204_M$ (collectively referred to herein as entrance ports 204). As shown, the chamber covers 114 inhibit fluid flow between the ports 202 and the agent chambers 110 and between the agent chambers 110 and the ports 204 when the chamber covers 114 are closed. Fluid can flow between the ports 202 and the agent chambers 110 and the ports 204 and the sample channel $106_1$ when the chamber covers 114 are open.

In FIG. 2, a sample 206 is shown traversing the sample channel $106_1$ and an agent 208 is being moved from the agent chamber $110_1$ into the sample channel $106_1$. In this embodiment, the exit ports 204 include one-way valves $210_1$, ..., $210_M$ (collectively referred to herein as valves 204). The valves 210 each include two flaps that allow the agent 208 to flow out of the exit ports 204 and into the sample channel $106_1$ and mitigates flow of a fluid from the sample channel $106_1$ into the exit ports 204 and agent chambers 110. As shown, in this embodiment, the valve $210_1$ is open, allowing the agent 208 in the chamber $110_1$ to egress, and the valve $210_1$ is closed, inhibiting the agent in the chamber $110_1$ from egressing. The illustrated valves 210 are configured to open in response to a suitable force on the valves 210 from a direction from the chambers 110.

Note that orientation of the agent chambers 110, the chamber covers 114, the entrance and exit port 202 and 204, and the pressure source 120 is provided for illustrative purposes and not limiting, and may be otherwise oriented. For example, the of the agent chambers 110, the chamber covers 114, and/or the entrance and exit port 202 and 204 can be located in the sample carrier 102 above, below or next to corresponding sample channels 106, and the pressure source 120 can be located above, below or next to the sample carrier 102.

Turning to FIG. 3, a cross sectional view through a single agent chamber $110_1$ of the sample carrier 102 along lines A-A of FIG. 2 is illustrated.

The cross sectional view shows the entrance port $202_1$ leading to the chamber cover $114_{11}$, which is located at an entrance opening $302_1$ of the agent chamber $110_1$ into a first portion $304_1$ of two portions $304_1$ and $304_2$ of an agent chamber $110_1$. The second portion $304_2$ of two portions $304_1$ and $304_2$ the agent chamber $110_1$ leads an exit opening $302_2$ of the agent chamber $110_1$. The chamber cover $114_{12}$ is located at the exit opening $302_2$, which leads to the exit port $204_1$.

In this embodiment, the chamber covers $114_{11}$ and $114_{12}$ are part of a middle layer 306 that is disposed between a top layer 308 (which includes the entrance and exit ports $202_1$ and $204_1$) and a bottom layer 310 (which includes the agent chamber $110_1$). The middle layer 306 may be a two dimensional plane sandwiched between the first and second layers 308 and 310. Alternatively, the middle layer 306 may include a plurality of sub-sections respectively corresponding to the individual chamber covers 114.

In FIG. 3, the agent chamber $110_1$ is "U" shaped, with the first portion $304_1$ corresponding to one leg of the "U" and being larger than the second portion $304_2$, which corresponds to the other leg of the "U". In another embodiment, the first portion $304_1$ and the second portion $304_2$ are about the same size. In yet another embodiment, the first portion $304_1$ is smaller than the second portion $304_2$. In still another embodiment, the agent chamber $110_1$ is otherwise shaped, for example "V," "W," and/or otherwise shaped.

Next at FIG. 4, an example chamber opener 118 is illustrated. In the illustrated embodiment, the chamber opener 118 utilizes an electromagnetic radiation source 402 of an optical detection system 404 (only shown in part in FIG. 4) of the sample processing apparatus 100 which is used with an electrophoresis processing station $108_1$ of the sample processing apparatus 100, where the sample processing apparatus 100 includes a DNA analyzer.

The illustrated electromagnetic source 402 includes a laser configured to transmit a laser beam within a pre-determined electromagnetic radiation range. In one embodiment, the source 402 transmits a generally narrow laser beam (e.g., 10 to 100 micron diameter) having a wavelength of about 488 nanometer (±5 nm) and a power rating of about 200 (~160) milliwatts. Other sources, including non-laser sources such as a light emitting diode (LED), an incandescent light, etc. are also contemplated herein.

A beam reflector 406 such as a mirror or other reflector is used to direct the laser light. The reflector 406 is movably mounted, and a reflector controller 409 is configured to controllably rotate, pivot, tilt or translate the reflector 406 to scan the laser. In one non-limiting instance, the reflector 406 is mounted on an end of a rotary shaft and the controller 409 controls an electromagnetic device such as a galvanometer that deflects the shaft to move the reflector 406.

For the electrophoresis processing station $108_1$, the reflector controller 409 causes the reflector 406 to rotate from a position 408 to a position 410 which moves a transmission path 412 along a scan path 414, which scans the laser across the sample channels 106 of the sample carrier 102. For opening chamber covers 114 in connection with the processing station $108_2$, the reflector controller 409 causes the reflector 406 to rotate to position 416 and position 418, which directs the transmission path at the reflectors 420 and 422, which directs the transmission path at the chamber covers $114_{12}$ and $114_{11}$.

In the illustrated embodiment, a single reflector is used to direct the transmission path to the chamber cover $114_{11}$ and a single reflector is used to direct the transmission path to the chamber cover $114_{12}$. In another embodiment, more than one reflector is used to direct the transmission path to a particular cover 114. Furthermore, one or more lenses can be used to focus the laser beam on the chamber covers 114.

In addition, a source other than the source 402 can be utilized. In one instance, a dedicated source can be used for each chamber cover 114. In another instance, the dedicated source can be used for sets of corresponding chamber covers 114. In another instance, the dedicated source can be used for all of the chamber covers 114. In yet another instance, a splitter can be used to split a source (e.g., the source 402 or other source) to create multiple beams for illuminating different chamber covers 114.

FIGS. 5-10 visually illustrate opening of chamber covers 114 and moving an agent in connection with a single agent chamber 110.

Figure 5:
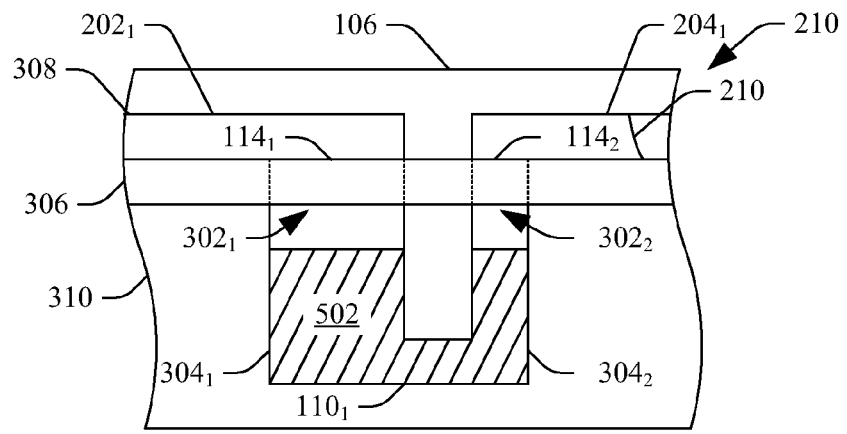
FIGS. 5-10 schematically illustrate an example in which the agent chamber cover opener is utilized to open at least one agent chamber cover of an agent chamber and the fluid mover is utilized to move an agent out of the agent chamber to a sample channel of the sample processing apparatus.

Initially referring to FIG. 5, the agent chamber $110_1$ includes an agent 502, and the chamber covers $114_1$ and $114_2$ are intact, inhibiting fluid from entering the chamber $110_1$ and the agent 502 from leaving the chamber $110_1$. In this example, the agent 502 is to be moved into a sample channel 106 at a predetermined step in the sample processing process. In one instance, the sample carrier 102 comes pre-loaded with the agent 502. In another instance, a user fills the chamber 110 with the agent 502. For example, a syringe or other device can be used to add the agent 502 to the agent chamber $110_1$.

Figure 6:
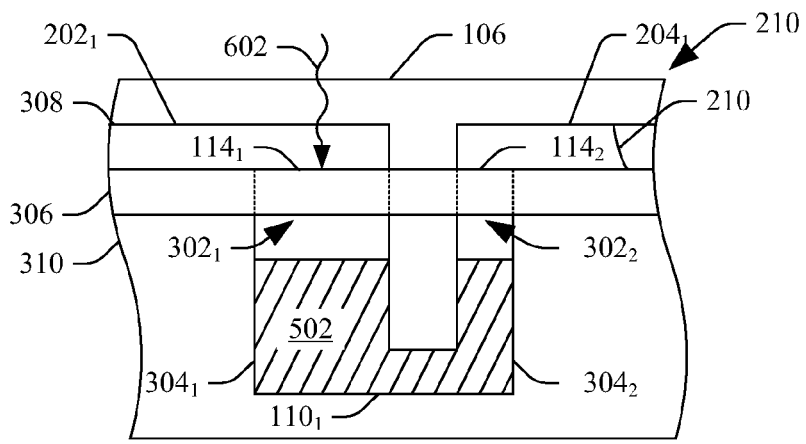

Turning to FIG. 6, the source 402 (FIG. 4) of the optical detection system 404 (FIG. 4) or other source is actuated to transmit a signal 602, which is directed by the reflector 406 (FIG. 4) (and/or one or more other reflectors and/or one or more lenses) at the chamber cover $114_1$. The signal 602 is directed at the chamber cover $114_1$ for a pre-determined time period of sufficient duration to allow the signal 602 to structurally compromise (e.g., break, melt, etc.) the chamber cover $114_1$. Where chamber covers $114_1$ for multiple chambers $110_1$ corresponding to multiple sample channels $106_1, \ldots, 106_M$, are to be opened, the chamber covers $114_1$ can be sequentially and/or concurrently opened.

Figure 7:
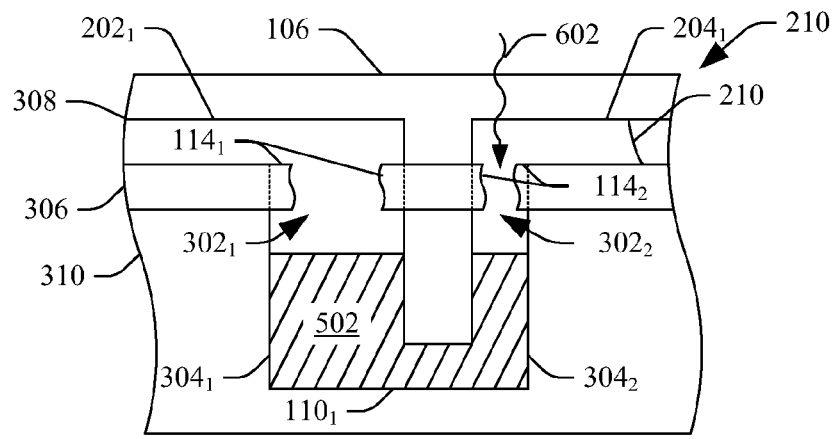

Next at FIG. 7, the source 402 (FIG. 4) of the optical detection system 404 (FIG. 4) or other source is actuated to transmit the signal 602, which is directed by the reflector 406 (FIG. 4) (and/or one or more other reflectors) at the chamber cover $114_2$. Again, the signal 602 is directed at the chamber cover $114_2$ for a pre-determined time period of sufficient duration to allow the signal 602 to structurally compromise (e.g., break, melt, etc.) the chamber cover $114_2$. Likewise, where chamber covers $114_2$ for multiple chambers $110_1$ corresponding to multiple sample channels $106_1, \ldots, 106_M$, are to be opened, the chamber covers $114_2$ can be sequentially and/or concurrently opened. FIG. 7 shows both of the chamber covers $114_1$ and $114_2$ open.

Where the signal 602 is split or where multiple sources are employed, the chamber cover 114$_1$ and 114$_2$ can be individually or concurrently opened.

Figure 8:
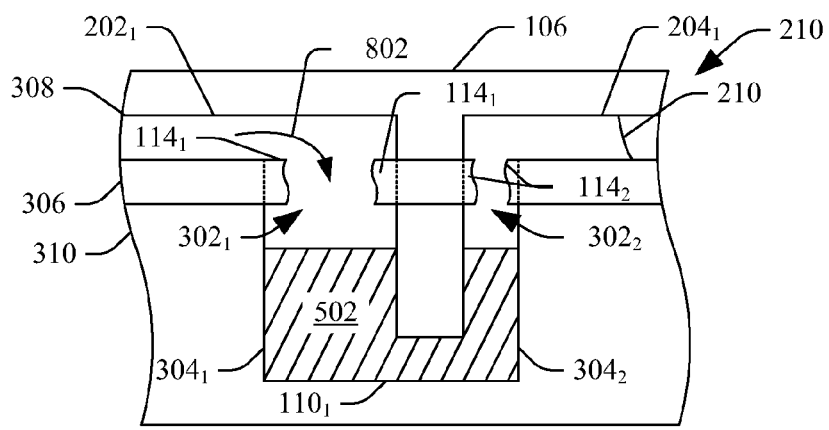
Figure 9:
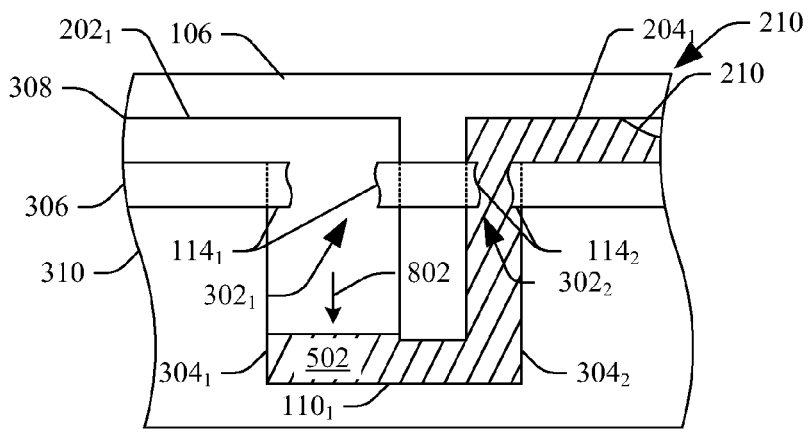
Figure 10:
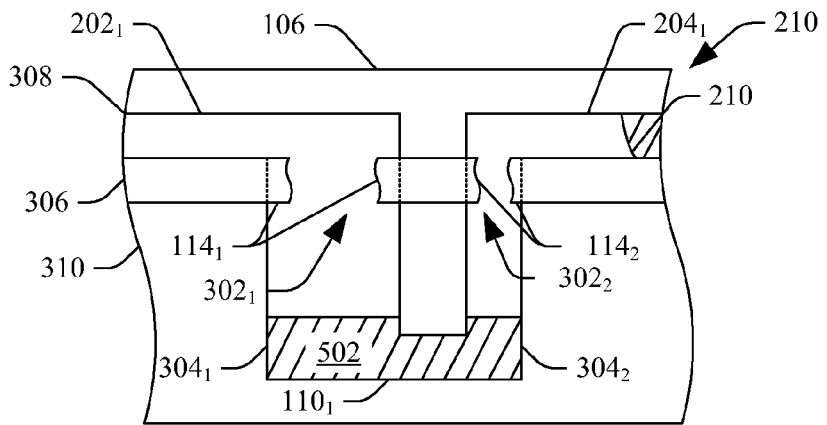
Figure 11:
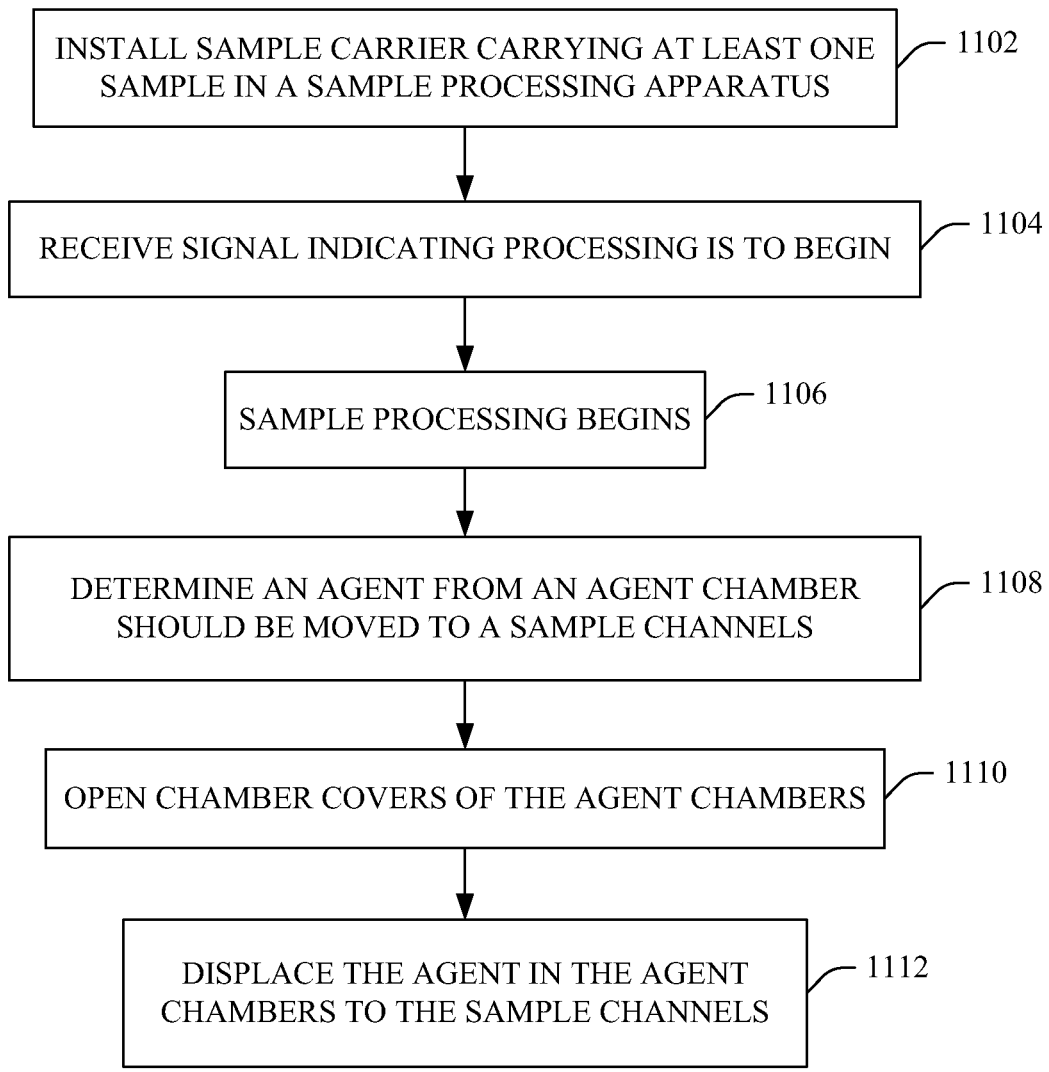
FIG. 11 illustrates an example method.

Turning to FIG. 8, the fluid mover 120 (FIG. 1) supplies pressurized air 802 to the entrance port 202$_1$ which travels through the entry opening 302$_1$ into the chamber portion 304$_1$. In FIG. 9, the pressurized air 802 exerts a force on the agent 502 that causes the agent 502 to displace from the chamber portion 304$_1$ into the chamber portion 304$_2$ through the exit opening 302$_2$ (and opening the valve 210) and out of the exit port 204 to the sample channel 106. In FIG. 10, the fluid mover 120 (FIG. 1) has removed the pressurized air 802. As a consequence, any of the agent 502 in the exit port 302$_1$ flows from the exit port 302$_1$ back into the chamber 110, and the valve 210 closes, preventing fluid in the sample channel 106 from entering the chamber 110.

Note that in this example, the volume of the agent 502 in the chamber 110 is in excess of the volume of the agent 502 moved into the sample channel 106. In one instance, this helps prevent moving air bubbles into the sample channel 106. By way of example, in FIG. 9, the level of the agent 502 in the first region 304$_1$ does not reach a level low enough for an air bubble to move to the second region 304$_2$ and out through the exit port 302$_1$ to the sample channel 106. In other embodiments, more (including all) or less of the agent 502 is moved into the sample channel 106.

It is to be appreciated that by first opening the chamber covers 114 and then supplying pressurized air (e.g., five (5) psig) to move the agents mitigates prematurely moving an agent from an agent chamber 110 and into a sample channel 106 in a configuration in which the pressured air is used to both open the chamber covers 114 and move the agents, where the chamber covers 114 may not open concurrently. As such, with the approach discussed herein, the agents can be moved concurrently, which may facilitate uniform processing of samples across multiple sample channels 106.

Variations and/or other embodiments are contemplated.

In a variation of the above, the chamber opener 118 is used to weaken (and not open) the agent covers 114. This can be achieved, for example, by reducing the output power of the source 402, reducing the amount of time the source 402 illuminates the covers 114, and/or otherwise. The fluid mover 120 then supplies low pressure (e.g., five (5) psig) which breaks open the weakened chamber covers 114, and the fluid mover 120 moves the agent in the agent chambers 110 as discussed herein or otherwise.

In another embodiment, the fluid mover 120 produces a signal that raises a temperature of the agent 502 in the chamber 110$_1$, causing the agent to expand and/or boil such that the expanding or boiling agent 502 breaks the chamber cover 114$_2$, allowing the expanding or boiling agent 502 to flow out of the exit port 302$_1$ to the sample channel 106. With this embodiment, the chamber opener 118 can be omitted.

In yet another example, the middle layer 306 (FIG. 3) includes a metal film in thermal communication with the chamber cover 114$_1$. A voltage is applied across terminals of the metal film, and the metal film dissipates heat, raising the temperature of the agent 502 in the chamber 110$_1$, causing the agent to expand and/or boil such that the expanding or boiling agent 502 breaks the chamber cover 114$_2$, allowing the expanding or boiling agent 502 to flow out of the exit port 302$_1$ to the sample channel 106. Likewise, with this embodiment, the chamber opener 118 can be omitted.

In yet another example, a bladder or balloon is included in to the chamber 110$_1$, and the bladder is expanded via pressurized air, heat, etc., and the expanding bladder or balloon physically contacts the agent 502, displacing the agent 502 from the first region 304$_1$ to the second region 304$_2$, causing the chamber cover 114$_2$ to break, allowing the agent 502 to flow out of the exit port 302$_1$ to the sample channel 106.

In another embodiment, the agent is moved from the agent chamber to another region of the sample carrier 102 other than the sample channel 106. In another embodiment, the approaches described herein can be used to move a sample through the sample channel 106. That is, the material in the chamber 110$_1$ may be the sample being processed or a material that can be used to move the sample. For example, pressurized air and/or heat can be used as discussed herein to move a fluid such as a gel that fills the electrophoresis portion of the at least one sample channels.

In other embodiments, the chamber opener 118 uses sound, radio frequency, ultrasounds, visible light, infrared radiation, and/or other approach for opening or weakening the chamber covers 114.

FIG. 11 illustrates an example for moving an agent from an agent chamber to a sample channel.

It is to be understood that the following acts are provided for explanatory purposes. In another embodiment, one or more acts can be added and/or one or more acts can be removed. In addition, the order of one or more of the acts can be different. Furthermore, one or more of the acts can occur concurrently.

At 1102, a sample carrier with multiple sample channels respectively carrying different samples is installed in connection with a sample processing apparatus.

At 1104, a signal indicating processing is to begin is received.

At 1106, sample processing begins.

At 1108, it is determined that agent from agent chambers are to be moved into corresponding sample channels for processing the samples.

At 1110, the chamber opener is actuated to open the chamber covers corresponding to the agent chambers as discussed herein.

At 1112, the fluid mover is actuated to move the agents from the agent chambers to the sample channels as discussed herein.

Acts 1108 to 1112 are repeated as needed, if needed.

The above acts may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention can be construed as including all such modifications and alterations, including insofar as they come within the scope of the appended claims and the equivalents thereof.

What is claimed is:

1. A sample processing apparatus, comprising:

a sample carrier receiving region configured to receive a sample carrier, wherein the sample carrier includes at least one sample channel carrying at least one sample, at least one agent chamber carrying at least one agent to be moved to the at least one sample channel to facilitate processing of the at least one sample, and the at least one agent chamber includes at least one chamber cover covering at least one opening of the at least one agent chamber, inhibiting flow of the at least one agent from the at least one agent chamber to the at least one sample channel;

an optical detection system, including: an electromagnetic radiation source configured to transmit electromagnetic radiation; a first beam reflector configured to reflect the transmitted electromagnetic radiation, producing reflected electromagnetic radiation; and a beam reflector controller that rotates the first beam reflector, which scans the reflected electromagnetic radiation across the at least one sample channel, which facilitates opening the at least one chamber cover, and a fluid mover that moves the agent out of the at least one agent chamber after the at least one chamber cover is opened and into the at least one sample channel.

2. The sample processing apparatus of claim 1, wherein the reflected electromagnetic radiation structurally compromises the at least one chamber cover.

3. The sample processing apparatus of claim 1, wherein the reflected electromagnetic radiation melts the at least one chamber cover.

4. The sample processing apparatus of claim 1, wherein the reflected electromagnetic radiation weakens the at least one chamber cover.

5. The sample processing apparatus of claim 1, wherein the first beam reflector includes at least one of one or more lenses or mirrors.

6. The sample processing apparatus of claim 1, the optical detection system, further including:

a second beam reflector, wherein the beam reflector controller rotates the first beam reflector to direct the reflected electromagnetic radiation at the second beam reflector, which directs the reflected electromagnetic radiation at the at least one chamber cover.

7. The sample processing apparatus of claim 1, wherein the fluid mover supplies pressurized air to move the agent out of the at least one agent chamber after the chamber cover is opened and into the at least one sample channel.

8. The sample processing apparatus of claim 7, wherein the fluid mover supplies pressurized air in a range from three pounds per square inch to eight pounds per square inch.

9. The sample processing apparatus of claim 1, wherein the reflected electromagnetic radiation heats the at least one agent in the at least one agent chamber, expanding the agent, which displaces the agent from the at least one agent chamber to the at least one sample channel.

10. The sample processing apparatus of claim 9, wherein the optical detection system includes a resistive element that dissipates heat in response to a voltage being applied across the element, and the dissipated heat is used to heat the agent.

11. The sample processing apparatus of claim 1, where the at least one chamber cover includes built-in tensile membrane stress, which assist the electromagnetic radiation source in the opening of the at least one chamber cover.

12. The sample processing apparatus of claim 1, wherein the reflected electromagnetic radiation only weakens and does not break the chamber cover, and the fluid mover applies a force to the agents in the at least one agent chambers to open the weakened chamber cover.

13. A method, comprising:

receiving a sample carrier in a sample carrier receiving region of a sample processing apparatus, wherein the sample carrier includes at least one sample channel configured to carry at least one sample, at least one agent chamber carrying at least one agent to be moved to the at least one sample channel to facilitate processing of the at least one sample, and the at least one agent chamber includes at least one chamber cover covering at least one opening of the at least one agent chamber, inhibiting flow of the at least one agent from the agent chamber to the at least one sample channel;

actuating an electromagnetic radiation source of an an optical detection system of the sample processing apparatus to transmit electromagnetic radiation at a beam reflector that reflects the transmitted electromagnetic radiation, producing reflected electromagnetic radiation;

rotating, with a beam reflector controller, the beam reflector to scan the reflected electromagnetic radiation across the at least one chamber cover to facilitate opening the at least one chamber cover, and actuating a fluid mover of the sample processing apparatus to move the at least one agent out of the at least one agent chamber after the chamber cover is opened and into the at least one sample channel of the sample carrier.

14. The method of claim 13, further comprising:

directing the electromagnetic radiation at the at least one chamber cover for a pre-determined time period, melting the at least one chamber cover to open the at least one chamber cover.

15. The method of claim 14, wherein the electromagnetic radiation is a laser beam.

16. The sample processing apparatus of claim 14, further comprising:

an electromagnetic device; and a rotary shaft, wherein the first beam reflector is mounted to the rotary shaft, and the beam reflector controller controls the electromagnetic device to deflect the rotary shaft, which moves the first beam reflector to scan the laser beam.

17. The method of claim 13, further comprising:

directing the electromagnetic radiation at the at least one chamber cover for a pre-determined time period, heating the agent which expands the agent, which breaks the at least one chamber cover to open the at least one chamber cover.

18. The method of claim 17, wherein the agent is a gel.

19. The method of claim 13, further comprising:

applying a voltage across a resistive element, wherein the resistive element dissipates heat, which heats the agent which expands the agent, which breaks the at least one chamber cover to open the at least one chamber cover.

20. The method of claim 13, further comprising:

expanding a bladder, wherein the expanding bladder displaces the agent from the at least one agent chamber.

* * * * *